United States Patent
Elledge

(10) Patent No.: US 7,235,488 B2
(45) Date of Patent: Jun. 26, 2007

(54) IN-SITU CHEMICAL-MECHANICAL PLANARIZATION PAD METROLOGY USING ULTRASONIC IMAGING

(75) Inventor: Jason B Elledge, Boise, ID (US)

(73) Assignee: Micron Technology, Inc., Boise, ID (US)

( * ) Notice: Subject to any disclaimer, the term of this patent is extended or adjusted under 35 U.S.C. 154(b) by 339 days.

(21) Appl. No.: 10/231,801

(22) Filed: Aug. 28, 2002

(65) Prior Publication Data

US 2004/0043521 A1    Mar. 4, 2004

(51) Int. Cl.
*H01L 21/461* (2006.01)
(52) U.S. Cl. .................................... 438/690; 438/691
(58) Field of Classification Search ......... 438/690–693
See application file for complete search history.

(56) References Cited

U.S. PATENT DOCUMENTS

| | | | |
|---|---|---|---|
| 5,655,951 A | 8/1997 | Meikle et al. | |
| 5,690,540 A | 11/1997 | Elliott et al. | |
| 5,736,427 A | 4/1998 | Henderson | |
| 5,738,567 A | 4/1998 | Manzonie et al. | |
| 5,829,439 A * | 11/1998 | Yokosawa et al. | 600/461 |
| 5,879,226 A | 3/1999 | Robinson | |
| 5,972,792 A | 10/1999 | Hudson | |
| 5,976,000 A | 11/1999 | Hudson | |
| 6,045,434 A * | 4/2000 | Fisher et al. | 451/6 |
| 6,062,958 A | 5/2000 | Wright et al. | |
| 6,194,231 B1 | 2/2001 | Ho-Cheng et al. | |
| 6,213,845 B1 | 4/2001 | Elledge | |
| 6,244,944 B1 | 6/2001 | Elledge | |
| 6,264,532 B1 * | 7/2001 | Meloni | 451/6 |
| 6,273,800 B1 | 8/2001 | Walker et al. | |
| 6,482,077 B1 | 11/2002 | Doan et al. | |
| 6,798,529 B2 * | 9/2004 | Saka et al. | 356/630 |

\* cited by examiner

*Primary Examiner*—H. Jey Tsai
(74) *Attorney, Agent, or Firm*—Fish & Neave IP Group Ropes & Gray LLP

(57) ABSTRACT

Chemical-mechanical planarization (CMP) apparatus and methods for detecting polishing pad properties using ultrasonic imaging is presented. An ultrasonic probe assembly transmits ultrasonic signals onto the surface of a polishing pad during a CMP process. Reflected ultrasonic signals are collected and analyzed to monitor polishing pad properties in real-time. This allows CMP process adjustments to be made during the CMP process.

41 Claims, 6 Drawing Sheets

IN-SITU CHEMICAL-MECHANICAL PLANARIZATION PAD METROLOGY USING ULTRASONIC IMAGING

BACKGROUND OF THE INVENTION

This invention relates to apparatus and methods of chemical-mechanical planarization using ultrasonic imaging. More particularly, this invention relates to a chemical-mechanical planarization pad metrology apparatus that transmits an ultrasonic signal onto the surface of a polishing pad to monitor polishing pad properties in real-time.

Fabricating integrated circuit devices is a complex multi-step process that creates structures with various electrical properties to form a connected set of devices. Multiple layers of conducting, semiconducting, dielectric, and insulting materials are deposited on a substrate during integrated circuit device fabrication. As these devices become smaller and more densely packed, more levels of photolithography and additional processing steps are often required.

Often, imperfect substrate fabrication and imperfect integrated circuit layer deposition result in formation of undesirable topography (e.g., recesses, protrusions, scratches, etc.) on the substrate and on one or more of the deposited layers. Because undesirable topography can compromise the integrity of an integrated circuit device (e.g., a topographical recess in a dielectric layer can impose step coverage problems for the deposition of another integrated circuit layer, and undesirable topology can cause depth of focus issues during photolithography), the substrate and each deposited layer of an integrated circuit device are preferably planarized (i.e., made level) before additional layers of integrated circuit material are deposited.

A common technique used to planarize the surface material of an integrated circuit wafer is chemical-mechanical planarization ("CMP"). Known CMP processes are used to remove undesirable topology from layers of integrated circuit material. The rotating polishing pad mechanically polishes (i.e., removes undesirable topography from) the surface material of the integrated circuit wafer. Concurrently, a fluid-based chemical (i.e., a chemical polishing "slurry") is dispensed onto the surface of the polishing pad to facilitate the removal of undesirable topography. Chemical polishing slurry may react with the integrated circuit material. That is, the slurry chemically weakens surface material of the wafer so that the surface is more easily removed by the mechanical abrasion of the polishing pad. Chemical polishing slurry may also be an inert liquid applied to the polishing pad. The inert liquid facilitates the removal of mechanically-ground integrated circuit material.

As device dimensions continue to scale down, CMP processes become more critical in the process flow. For example, polishing actions should be performed such that scratches or other defects do not appear on the surface of the polished integrated circuit wafer. Furthermore, in order to achieve uniform planarity, a constant polishing rate should be maintained. Thus, polishing pad maintenance plays a significant role in diminishing the drawbacks of the CMP process.

It has been shown that polishing pad properties, such as pad roughness (or texture), pad groove depth (which determines pad wear and pad erosion), pad density, pad thickness, and elastic modulus, influence CMP removal rates and uniform planarity. However, information that relates polishing pad properties to polishing performance is sparse because of inadequate measurement techniques.

Currently, surface topography measurements are obtained using known optical systems, such as a laser scanning microscope. However, there are significant drawbacks with the use of a laser scanning microscope. First, the CMP pad must be cleaned and dried before it can be examined with the microscope, which is a time-consuming and inefficient process. Also, because scanning laser microscopes are cumbersome, the examination process is performed offline (i.e., outside of the CMP tool), which is also a time-consuming and inefficient process. Furthermore, because CMP pads are typically semi-translucent, scanning laser microscopes and other known optical systems have difficulty resolving scratches and polishing pad defects.

In view of the foregoing, it would be desirable to collect polishing pad data and transmit the collected data in real-time to a processor such that process adjustments may be made during a CMP process.

It would also be desirable to maximize wafer throughput (i.e., the number of wafers processed per unit of time) while determining and monitoring polishing pad properties.

It would further be desirable to provide an apparatus for in-situ CMP pad metrology that uses ultrasonic imaging.

SUMMARY OF THE INVENTION

It is an object of this invention to collect polishing pad data and transmit the collected data in real-time to a processor such that process adjustments may be made during a CMP process.

It is also an object of this invention to maximize wafer throughput while determining and monitoring polishing pad properties.

It is a further object of this invention to provide an apparatus for in-situ CMP pad metrology that uses ultrasonic imaging.

In accordance with this invention, an apparatus and method for polishing pad metrology using ultrasonic imaging is provided that determines and monitors polishing pad properties and allows real-time process adjustments to a CMP process.

In a preferred embodiment of the invention, ultrasonic imaging is performed by an ultrasonic probe assembly, which preferably includes an ultrasonic source and an ultrasonic detector. The ultrasonic probe assembly transmits ultrasonic signals onto the surface of a polishing pad. While some of the transmitted ultrasonic signals propagate through the polishing pad, other transmitted ultrasonic signals are reflected from the surface of the polishing pad and are collected by the ultrasonic detector. The reflected ultrasonic signals are analyzed in real time to provide real-time monitoring of the polishing pad as it polishes. For example, upon correlating the reflected ultrasonic signals with polishing pad position data from which the measurement was taken, contour maps and cross-sectional pad profiles can be obtained. Also, real-time pad properties, such as pad wear and pad erosion can be obtained from the reflected ultrasonic signals.

In some embodiments, the data collected while monitoring the polishing pad as it polishes may be transmitted to, for example, engineers, computer software, or apparatus that generates statistical process control (SPC) charts. Based at least in part on the collected data, real-time process adjustments may be made. For example, the process recipe may be automatically adjusted to compensate for pad wear or pad erosion, thus extending the life of a polishing pad and improving wafer throughput.

BRIEF DESCRIPTION OF THE DRAWINGS

The above and other objects and advantages of the invention will be apparent upon consideration of the following detailed description, taken in conjunction with the accompanying drawings, in which like reference characters refer to like parts throughout, and in which.

DETAILED DESCRIPTION OF THE INVENTION

The invention provides CMP pad metrology apparatus and methods for in-situ determination and monitoring of polishing pad properties using ultrasonic imaging during a CMP process.

Ultrasonic imaging uses a focused ultrasonic signal transmitted onto the surface of a polishing pad. While ultrasonic imaging is widely used in the medical industry (e.g., non-invasive imaging of a fetus) and in the aerospace industry (e.g., defect detection in structures), ultrasonic imaging can also be advantageously used in the semiconductor industry for monitoring polishing pad properties during a CMP process.

Ultrasonic imaging differs from other well-known optical imaging methods because it does not require sample preparation (e.g., polishing pads that are cleaned and dried) and because it provides a non-destructive method for determining physical properties, microstructure, and topography images. Ultrasonic probes are also portable and cost-effective. Even further, ultrasonic imaging can be applied to all states of matter except plasma. For example, unlike known optical imaging methods, propagation of an ultrasonic signal through a material is not affected by the material's transparency or opacity. Because polishing pads are typically semi-transparent, known optical imaging methods typically have difficulty resolving surface defects.

In accordance with the invention, apparatus and methods are provided for polishing pad metrology using ultrasonic imaging that determines and monitors polishing pad properties and allows real-time process adjustments to a CMP process.

Figure 1:
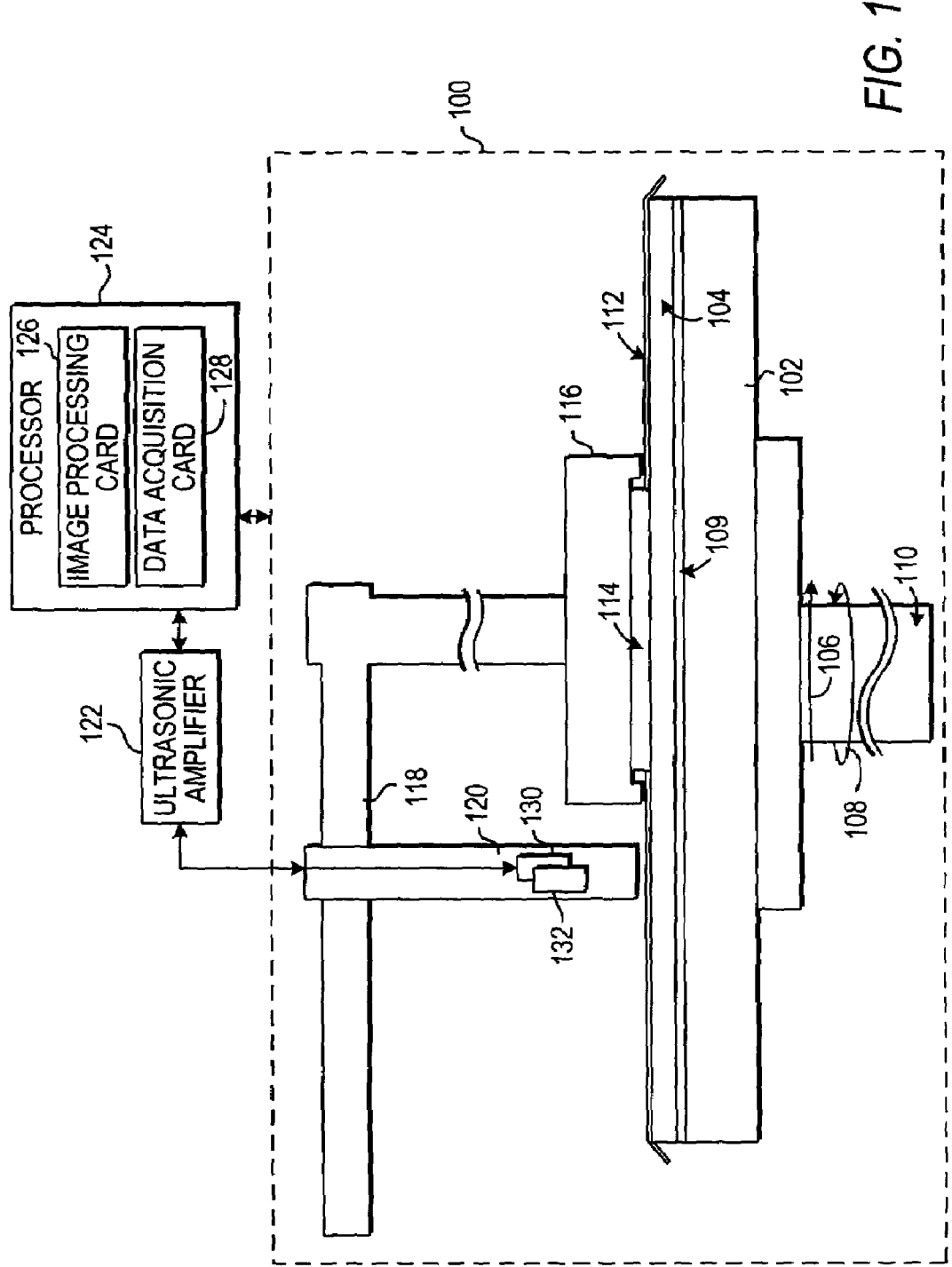
FIG. 1 is a schematic diagram of an embodiment of a CMP apparatus for in-situ monitoring of polishing pad properties according to the invention.

FIG. 1 illustrates an embodiment of CMP apparatus having ultrasonic imaging for in-situ monitoring of CMP pad properties in accordance with the invention. CMP apparatus 100 has a platen 102 and a polishing pad 104. Platen 102 and polishing pad 104 are driven by a drive assembly 110 to move with translation motions 106 and rotation motions 108. Polishing pad 104 may be a conventional polishing pad made from a relatively soft, thin, and porous material, such as polyurethane. Polishing pad 104 may also be an abrasive polishing pad with abrasive particles fixedly bonded to a suspension medium. CMP apparatus 100 may also have an underpad 109 attached to the surface of platen 102 for supporting polishing pad 104.

To planarize a substrate 114, a conditioning head assembly 116 presses substrate 114 against polishing pad 104 in the presence of fluid-based polishing chemical 112. As used herein, "substrate" includes a base layer (e.g., a silicon wafer, a semiconductor material, or an insulating material) and may include one or more integrated circuit layers deposited on the base layer. Conditioning head assembly 116 may be driven to move backwards and forwards by a conditioning arm 118. Platen 102 and conditioning head assembly 116 move relative to one another to translate substrate 114 across the surface of polishing pad 104. As a result, the rotating polishing pad 104 mechanically polishes (i.e., removes undesirable topography from) the surface material of substrate 114. Concurrently, a fluid-based polishing chemical 112 (i.e., a chemical polishing "slurry") is dispensed onto the surface of polishing pad 104. Chemical polishing slurry 112 may react with the surface of substrate 114. In other embodiments, chemical polishing slurry 112 may be an inert liquid applied to the polishing pad to facilitate the removal of undesirable topography. For example, deionized water applied to the interface between polishing pad 104 and substrate 114 may facilitate removal of mechanically-ground integrated circuit material.

CMP processes should consistently and accurately produce a uniformly planar surface on the substrate in order to precisely fabricate integrated circuit devices. However, polishing pad 104 typically wears unevenly as it is used, thus affecting its removal rate. The removal rate of integrated circuit material varies based at least in part on age and erosion (i.e., pad wear) of polishing pad 104. For example, polishing pad 104 may be substantially more worn at the center of the pad than at the edge of the pad. Performing a CMP process on a substrate with such a non-uniform polishing pad results in non-uniformly planarized substrates. Thus, polishing pad 104 is preferably "conditioned" as part of the CMP process in order to restore polishing pad 104 to its original removal rate. When polishing pad 104 can no longer be conditioned, polishing pad 104 should be replaced.

As repeated CMP processes are performed, the properties of polishing pad 104 should be observed. Such properties may include, for example, pad roughness (i.e., texture), pad groove depth (which determines pad depth and pad erosion), pad density, pad thickness, and elastic modulus. To monitor and determine these polishing pad properties, CMP apparatus 100 also includes an ultrasonic probe assembly 120 and a computer processor 124. Ultrasonic probe assembly 120 preferably has a diameter between about 3 millimeters and 50 millimeters. Processor 124 preferably has an image processing card 126 and a data acquisition card 128.

Although a single ultrasonic probe assembly 120 is shown, multiple ultrasonic probe assemblies may be positioned within CMP apparatus 100 to facilitate monitoring of polishing pad properties.

In one embodiment, ultrasonic probe assembly 120 has a conventional "contact" ultrasonic transducer, where the interface medium between polishing pad 104 and ultrasonic probe assembly 120 is a suitable liquid or liquid gel material. In an alternative embodiment, ultrasonic probe assembly 120 has a "non-contact" ultrasonic transducer, in which there is no interface medium (i.e., air/gas) between polishing pad 104 and ultrasonic probe assembly 120 (a vacuum exists).

Ultrasonic probe assembly 120 preferably includes an ultrasonic source 130 and an ultrasonic detector 132 for transmitting and receiving ultrasonic signals. Ultrasonic source 130 is configured to transmit an ultrasonic signal at an area on the surface of polishing pad 104 as substrate 114 is being polished. Note that transmitting and receiving ultrasonic signals may also be performed between polishing steps (e.g., between wafers or lots). Ultrasonic probe assembly 120 preferably contacts chemical polishing slurry 112. While chemical polishing slurry 112 may be any suitable slurry, chemical polishing slurry 112 is preferably deionized water to provide an interface medium which is easily controllable and repeatable (e.g., it can be maintained at a constant temperature, has well-known properties, and is readily available). Note that if ultrasonic probe assembly 120 has a "non-contact" ultrasonic transducer, ultrasonic probe assembly 120 is not in contact with chemical polishing slurry 112.

As shown in FIG. 1, ultrasonic probe assembly 120 is preferably fixed to conditioning arm 118. In other embodiments, ultrasonic probe assembly 120 may be fixed to other suitable structures within CMP apparatus 100, such as conditioning head assembly 116, a slurry arm (not shown), or an overhead fixed ring (not shown). Processor 124 may be configured to direct conditioning arm 118 to move backwards and forwards over the surface of polishing pad 104 during the CMP process. The advantage of fixing ultrasonic probe assembly 120 to conditioning arm 118 is that processor 124 can calculate the real-time position of ultrasonic probe assembly 120 based at least in part on the position of conditioning arm 118. Furthermore, because conditioning arm 118 moves backwards and forwards across the diameter of polishing pad 104, which preferably rotates at a constant velocity, processor 124 can determine real-time polishing pad properties for a substantial portion of polishing pad 104.

If desired, CMP apparatus 100 may include sensors (not shown) to obtain position data of ultrasonic probe assembly 120. The sensors may be fixed to conditioning arm 118 or another suitable structure. The sensors transmit position data to processor 124. In response to receiving position data from the sensors, processor 124 correlates the collected position data with the collected ultrasonic signals.

Ultrasonic source 130 transmits ultrasonic signals onto the surface of polishing pad 104. Some ultrasonic signals may be absorbed (e.g., into chemical polishing slurry 112). Some ultrasonic signals may propagate through polishing pad 104 and be subsequently reflected from platen 102. (Platen 102 is preferably a metal, such as aluminum, which is an excellent reflector of ultrasonic signals). Some ultrasonic signals may reflect off of polishing pad 104. In response to ultrasonic detector 132 receiving reflected ultrasonic signals, ultrasonic probe assembly 120 transmits the reflected ultrasonic signals to an ultrasonic amplifier 122, which amplifies the signals before processing. The amplified reflected ultrasonic signals are then transmitted to processor 124 to determine the polishing pad properties for a particular position on polishing pad 104.

Figure 2:
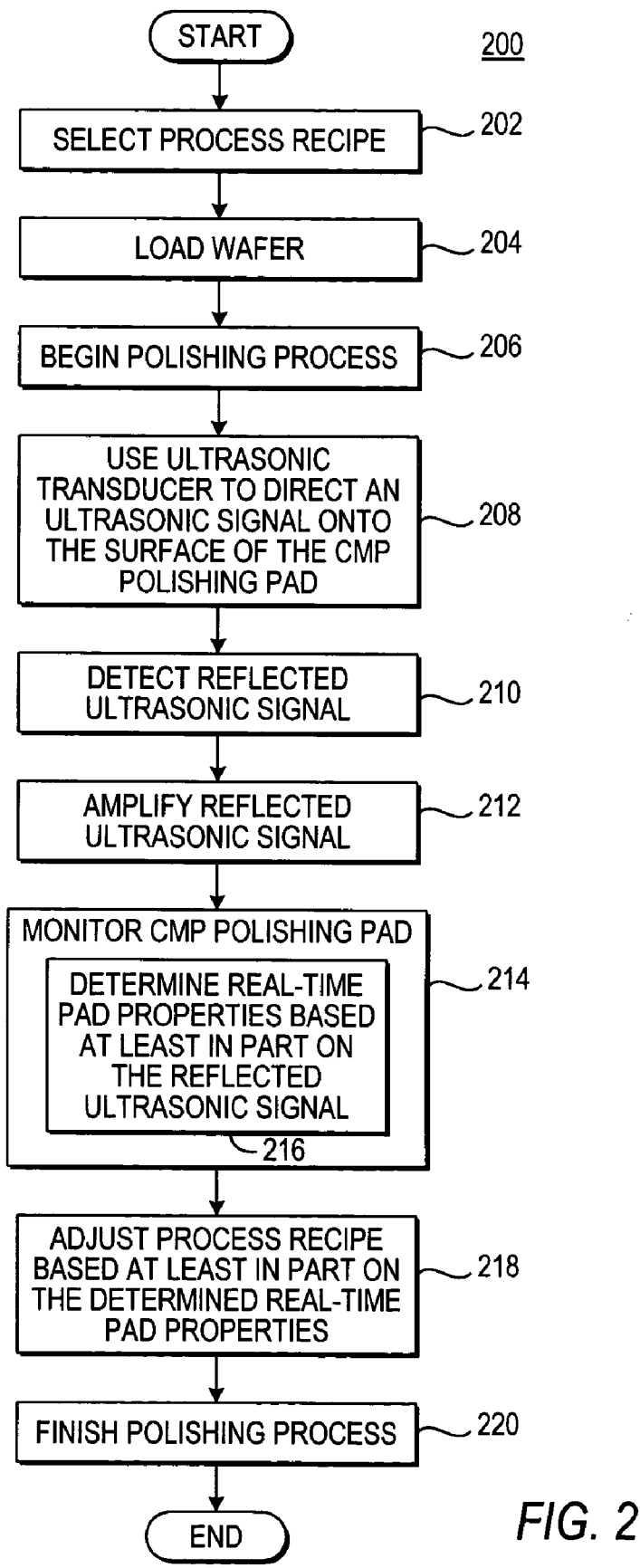
FIG. 2 is a flowchart of an embodiment of a method of monitoring polishing pad properties and then adjusting a CMP process based on the monitored properties according to the invention.

FIG. 2 shows an illustrative method 200 for determining and monitoring the properties of polishing pad 104 using ultrasonic probe assembly 120. At step 202, a user selects a process "recipe" using computer processor 124 or other suitable processor that can control CMP apparatus 100. As used herein, a process recipe includes a set of polishing parameters that can be varied to achieve control of the CMP process. Such a process recipe may be, for example, a polish recipe, a conditioning recipe, or any other suitable recipe. Process parameters may include, for example, the downward force applied by conditioning head assembly 116, the duration of the polishing operation performed by conditioning head assembly 116, the amount of backforce pressure used to secure substrate 114 to conditioning head assembly 116, the rotational velocity of conditioning head assembly 116, the oscillation of conditioning head assembly 116, or any other appropriate process parameters. In other embodiments, the user may manually create a customized process recipe. For example, the user may create a polishing recipe by inputting desired process parameters into processor 124.

In response to selecting or inputting a process recipe, substrate 114 is loaded onto CMP apparatus 100 at step 204. In some embodiments, CMP apparatus 100 may include a loading/unloading assembly (not shown). A cassette, holding at least one substrate, may be placed at the loading/unloading assembly. In response to CMP apparatus 100 detecting the presence of a cassette at the loading/unloading assembly, CMP apparatus 100 transfers substrate 114 from the cassette to conditioning head assembly 116 using a robot, a wafer transport arm, or other suitable wafer carrier.

At step 206, the CMP process begins. In particular, conditioning head assembly 116 holding substrate 114 is driven backwards and forwards over the surface of polishing pad 104. As a result, the rotating polishing pad 104 mechanically polishes the surface material of substrate 114. Concurrently, the chemical polishing slurry 112 is dispensed onto the surface of polishing pad 104.

While the CMP process is being performed (i.e., in-situ), ultrasonic source 130 transmits ultrasonic signals onto the surface of polishing pad 104 at step 208. In other embodiments, ultrasonic source 130 transmits ultrasonic signals onto the surface of polishing pad 104 after substrate 114 is polished (e.g., ex-situ). Some transmitted ultrasonic signals may be reflected from polishing pad 104, while others may propagate through polishing pad 104 and be subsequently reflected from platen 102. Ultrasonic detector 132 receives reflected ultrasonic signals at step 210. At step 212, the reflected ultrasonic signals are amplified by ultrasonic amplifier 122. The amplified signals are then transmitted to computer processor 124.

As computer processor 124 receives real-time reflected and amplified ultrasonic signals, computer processor 124 monitors the properties of polishing pad 104 at step 214. At substep 216, processor 124 determines real-time pad properties based at least in part on the reflected and amplified ultrasonic signals. For example, in response to receiving ultrasonic signals reflected from polishing pad 104 and ultrasonic signals reflected from platen 102, processor 124 may calculate the thickness of polishing pad 104. As shown in FIGS. 3–10, processor 124 may generate ultrasonic images and various graphs based at least in part on the collected ultrasonic signals.

As shown in FIGS. 3–10, ultrasonic probe assembly 120 preferably has the capability of resolving at least micron-sized polishing pad features, thus allowing processor 124 to measure pad properties, such as pad roughness (or texture), pad groove depth, and other physical pad properties.

Figure 3:
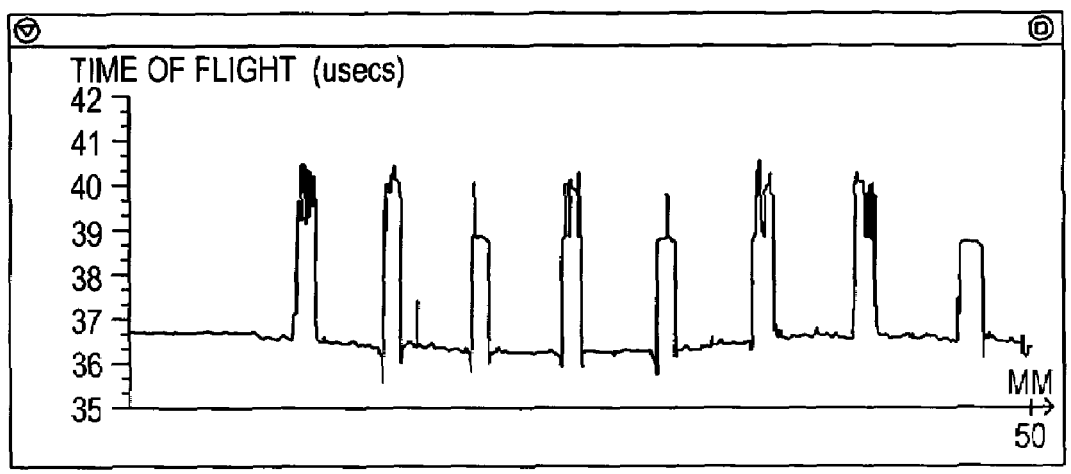
FIG. 3 is a graph of time of flight of ultrasonic signals versus polishing pad position for a polishing pad.

FIG. 3 shows the measured round-trip travel time (i.e., time of flight) of ultrasonic signals for a polishing pad versus position for a non-contact ultrasonic signal transmitted over 50 millimeters of the polishing pad. From the graph shown, processor 124 can determine the thickness of the polishing pad and pad groove depth. Processor 124 can also create a cross-sectional profile of the polishing pad.

Figure 4:
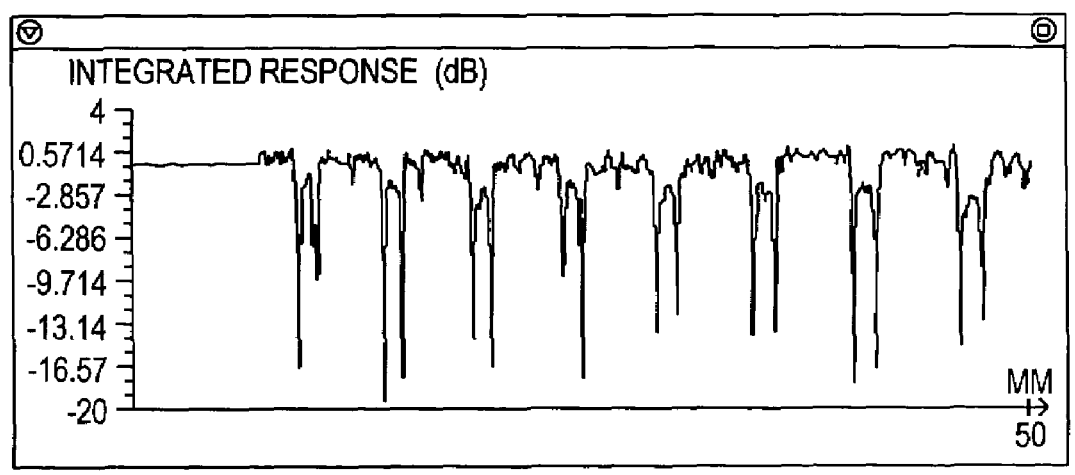
FIG. 4 is a graph of reflectivity versus polishing pad position for a polishing pad.

FIG. 4 shows a graph of reflectivity versus position for a non-contact ultrasonic signal transmitted over 50 millimeters of the polishing pad. Reflectivity is determined by calculating the area underneath a particular transmission or reflected peak. In FIG. 4, the higher the reflectivity, the smoother the surface. Thus, FIG. 4 illustrates the surface roughness of the polishing pad.

Figure 6:
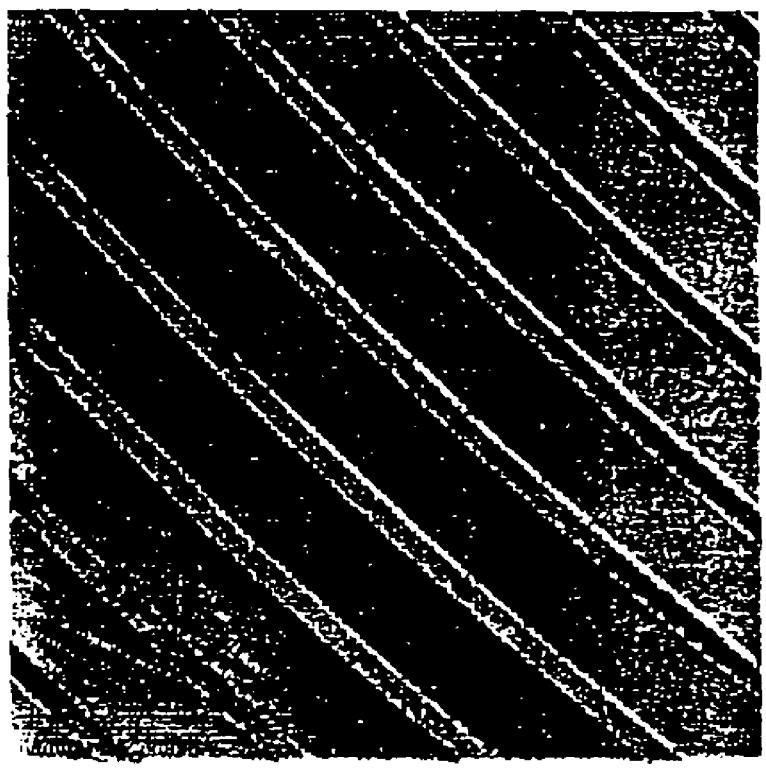
FIG. 6 is a time of flight surface profile image created from collected position data and time of flight data of a polishing pad.
Figure 5:
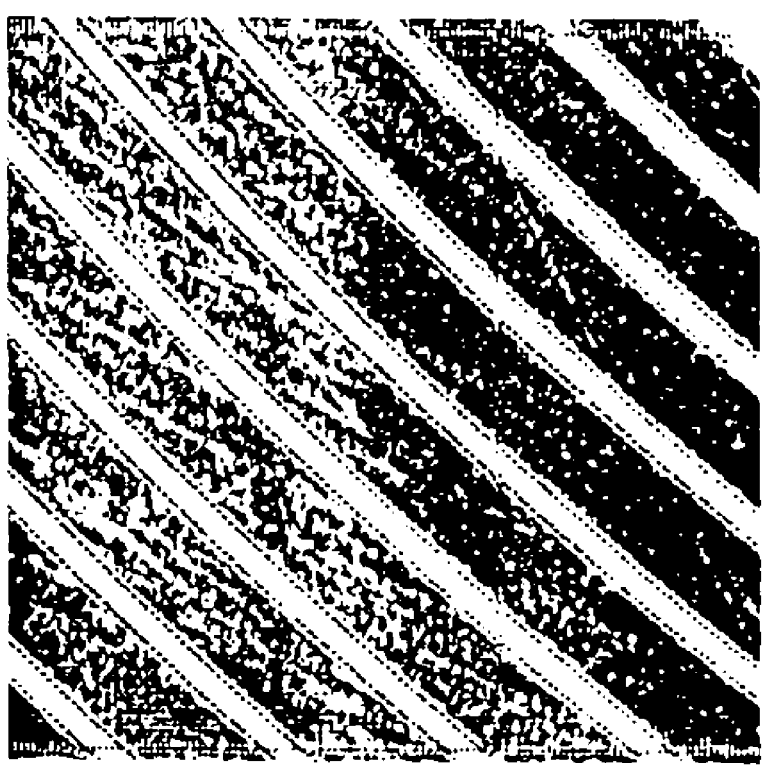
FIG. 5 is a reflection image of the surface of a polishing pad.
Figure 7:
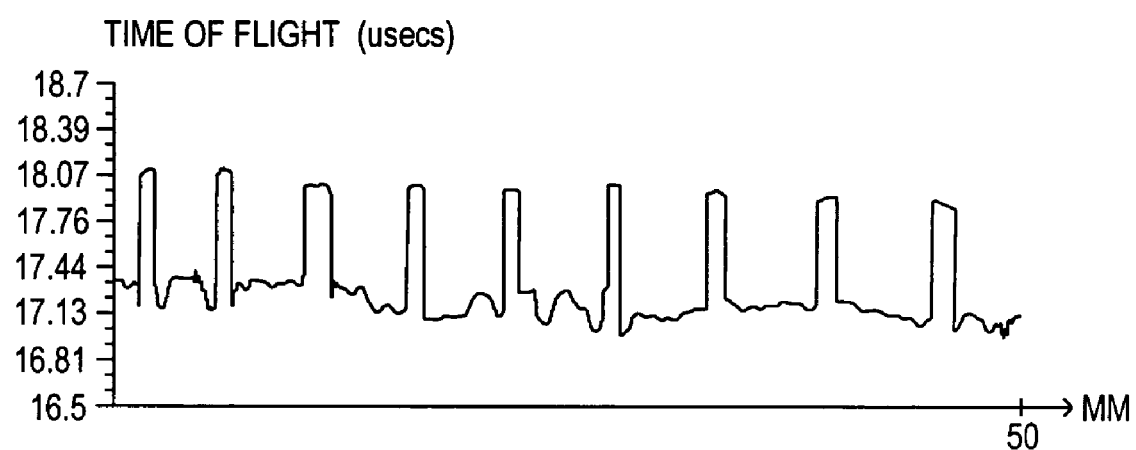
FIG. 7 is a graph of time of flight of the ultrasonic signals versus polishing pad position for a polishing pad immersed in deionized water.
Figure 8:
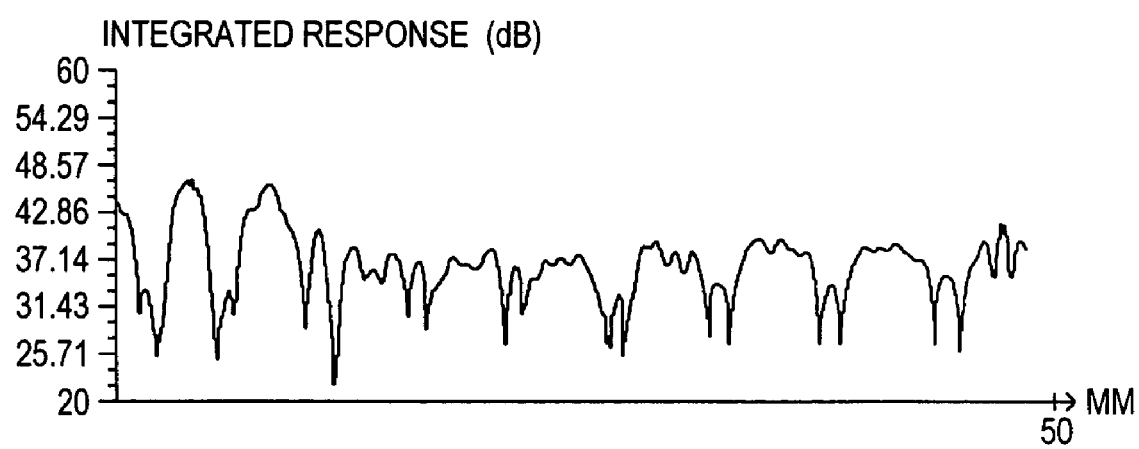
FIG. 8 is a graph of reflectivity versus polishing pad position for a polishing pad immersed in deionized water.
Figure 10:
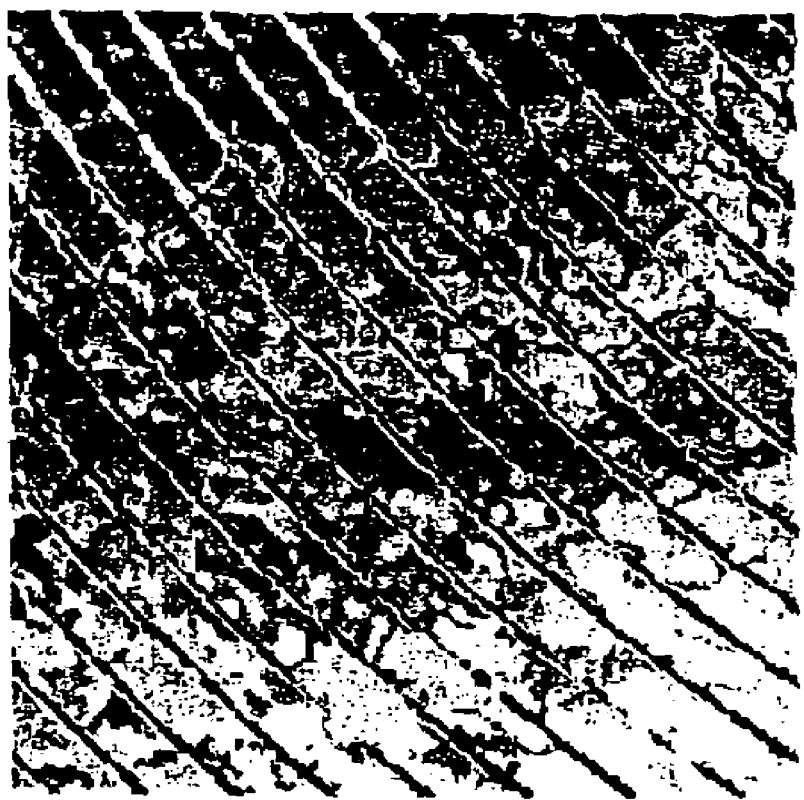
FIG. 10 is a time of flight surface profile image created using collected position data and time of flight data of a polishing pad immersed in deionized water.
Figure 9:
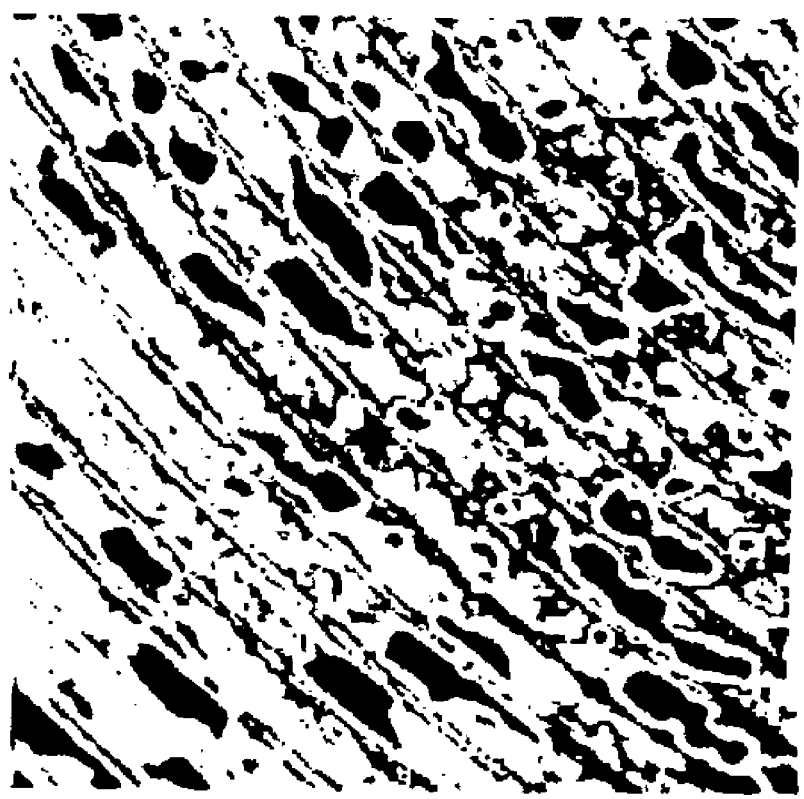
FIG. 9 is a reflection image of the surface of a polishing pad immersed in deionized water.

FIGS. 5 and 6 show a reflection image and a time of flight surface-profile image generated using position data and time of flight measurements. At a position along the scan, processor 124 estimates the depth of any feature that reflects the ultrasonic signal based at least in part on the time of flight of the ultrasonic signal. The ultrasonic detector operates with a time gate chosen so that its output indicates the amplitude of the ultrasonic signal reflected from the polishing pad at that particular position. Once the scan has been completed, processor 124 processes the position data and the associated depth and amplitude data into a single three-dimensional graph that shows both depth and amplitude as functions of position. In particular, FIGS. 5 and 6 provide a real-time topography image of the polishing pad.

Note that while FIGS. 3–6 were performed using a non-contact transducer (i.e., no interface medium), the ultrasonic probe assembly may also resolve polishing pad features while the polishing pad is immersed in an interface medium. For example, FIGS. 7–10 show a time of flight versus position graph, a reflectivity versus position graph, a reflection image, and a time of flight surface profile image, respectively, for a polishing pad immersed in deionized water.

Returning to FIG. 2, in response to processor 124 monitoring the properties of polishing pad 104, processor 124 may automatically adjust the process recipe (selected at step 202) based at least in part on the determined real-time pad properties. Automatically adjusting the process recipe improves throughput while optimizing polishing parameters. For example, processor 124 may automatically adjust the downward polish force or other polishing parameters to compensate for pad wear. Processor 124 may also notify the user when polishing pad 104 requires changing (e.g., based on pad wear monitoring).

The determined real-time pad properties (e.g., surface topography maps, pad thickness measurements, etc.) may also or instead be transmitted to the user. Alternatively, statistical process control (SPC) charts may be generated based on the pad properties. The user can then manually adjust the process recipe.

Although the invention is described herein in terms of chemical-mechanical planarization, the invention is also applicable to mechanical planarization of substrates.

Thus it is seen that ultrasonic signals may be used with CMP apparatus to determine and monitor polishing pad properties and to provide real-time process control. One skilled in the art will appreciate that the invention can be practiced by other than the described embodiments, which are presented for purposes of illustration and not of limitation, and the invention is limited only by the claims which follow.

I claim:

1. A method of monitoring chemical-mechanical polishing pads, the method comprising:
   transmitting ultrasonic signals onto the surface of a polishing pad using a contact ultrasonic transducer, wherein the ultrasonic signals are transmitted onto the surface of the polishing pad through a chemical polishing slurry and a portion of the ultrasonic signals are reflected;
   detecting the reflected ultrasonic signals; and
   processing the reflected ultrasonic signals, wherein the processing comprises measuring the reflectivity of the surface of the polishing pad to determine roughness of the polishing pad.

2. The method of claim 1 wherein the processing comprises generating a surface topography image of the polishing pad based at least in part on the reflected ultrasonic signals.

3. The method of claim 1 further comprising automatically adjusting a chemical-mechanical planarization process recipe based at least in part on the processed reflected ultrasonic signals.

4. A method of monitoring chemical-mechanical polishing pads, the method comprising:
   receiving a chemical-mechanical planarization process recipe;
   polishing a substrate with a polishing pad based on the received process recipe;
   transmitting ultrasonic signals onto the surface of the polishing pad while simultaneously polishing the substrate, wherein a portion of the ultrasonic signals are reflected;
   collecting the reflected ultrasonic signals;
   processing the reflected ultrasonic signals, wherein the processing comprises measuring the reflectivity of the surface of the polishing pad to determine roughness of the polishing pad; and
   adjusting the process recipe based at least in part on the determined roughness of the polishing pad.

5. The method of claim 4 wherein the process recipe is a polishing recipe.

6. The method of claim 4 wherein the process recipe is a conditioning recipe.

7. The method of claim 4 wherein the processing comprises generating a surface topography image of the polishing pad based at least in part on the reflected ultrasonic signals.

8. The method of claim 4 wherein the adjusting comprises using a computer processor to automatically adjust the process recipe based at least in part on the determined roughness of the polishing pad.

9. The method of claim 4 further comprising issuing a notification when the polishing pad requires replacement.

10. A method of monitoring chemical-mechanical polishing pads, the method comprising:
    receiving a chemical-mechanical planarization process recipe;
    polishing a substrate with a polishing pad based on the received process recipe;
    transmitting ultrasonic signals onto the surface of the polishing pad, wherein a portion of the ultrasonic signals are reflected;
    collecting position data for each transmitted ultrasonic signal substantially simultaneously while transmitting the ultrasonic signals;
    collecting the reflected ultrasonic signals;

correlating the collected position data with the reflected ultrasonic signals; and generating surface topography images using the collected position data and the reflected ultrasonic signals, wherein the generating comprises measuring the reflectivity of the surface of the polishing pad to generate the surface topography images.

11. A method of monitoring chemical-mechanical polishing pads, the method comprising:

receiving a chemical-mechanical planarization process recipe selected by a user;

polishing a substrate with a polishing pad based on the selected process recipe;

immersing the substrate and polishing pad in deionized water;

transmitting ultrasonic signals onto the surface of the polishing pad simultaneously while polishing, wherein a portion of the ultrasonic signals are reflected;

detecting the reflected ultrasonic signals; processing the reflected ultrasonic signals, wherein the processing comprises measuring the reflectivity of the surface of the polishing pad to determine roughness of the polishing pad; and adjusting the process recipe based at least in part on the determined roughness of the polishing pad.

12. The method of claim 11 wherein the adjusting comprises using a computer processor to automatically adjust the process recipe based at least in part on the determined roughness of the polishing pad.

13. The method of claim 11 wherein the process recipe is a polishing recipe.

14. The method of claim 11 wherein the process recipe is a conditioning recipe.

15. The method of claim 11 wherein the processing comprises generating a surface topography image of the polishing pad.

16. The method of claim 11 wherein the processing comprises generating a statistical process control chart.

17. A method of monitoring chemical-mechanical polishing pads, the method comprising:

receiving a chemical-mechanical planarization process recipe;

polishing a substrate with a polishing pad based on the selected process recipe;

transmitting ultrasonic signals onto the surface of the polishing pad simultaneously while polishing, wherein a portion of the ultrasonic signals are reflected;

detecting the reflected ultrasonic signals; processing the reflected ultrasonic signals, wherein the processing comprises measuring the reflectivity of the surface of the polishing pad to determine roughness of the polishing pad; and receiving adjustments to the process recipe during the polishing.

18. The method of claim 17 wherein the processing comprises generating a surface topography image of the polishing pad.

19. The method of claim 17 wherein the processing comprises generating a statistical process control chart.

20. A method of monitoring substrate polishing pads, the method comprising:

transmitting ultrasonic signals onto the surface of a polishing pad, wherein a portion of the ultrasonic signals are reflected;

detecting the reflected ultrasonic signals;

processing the reflected ultrasonic signals to monitor the polishing pad, wherein the processing comprises measuring the reflectivity of the surface of the polishing pad to generate a surface topography image of the polishing pad based at least in part on the reflected ultrasonic signals.

21. A method of monitoring substrate polishing pads, the method comprising:

receiving a process recipe;

polishing a substrate with a polishing pad based on the received process recipe;

transmitting ultrasonic signals onto the surface of the polishing pad while simultaneously polishing the substrate, wherein a portion of the ultrasonic signals are reflected;

collecting the reflected ultrasonic signals;

processing the reflected ultrasonic signals, wherein the processing comprises measuring the reflectivity of the surface of the polishing pad to determine physical properties of the polishing pad, wherein determining the physical properties comprises generating a surface topography image of the polishing pad based at least in part on the reflected ultrasonic signals; and adjusting the process recipe based at least in part on the determined physical properties of the polishing pad.

22. The method of claim 1 wherein the chemical polishing slurry comprises deionized water.

23. The method of claim 1 wherein the processing comprises generating a cross-sectional pad profile based at least in part on the reflected ultrasonic signals.

24. The method of claim 1 wherein the processing further comprises resolving approximately micron-sized properties of the polishing pad.

25. The method of claim 4 wherein the transmitting further comprises using a contact ultrasonic transducer to transmit ultrasonic signals onto the surface of the polishing pad through a chemical polishing slurry.

26. The method of claim 25 wherein the chemical polishing slurry comprises deionized water.

27. The method of claim 4 wherein the processing comprises generating a cross-sectional pad profile based at least in part on the reflected ultrasonic signals.

28. The method of claim 4 wherein the processing further comprises resolving approximately micron-sized properties of the polishing pad.

29. The method of claim 10 wherein the transmitting further comprises using a contact ultrasonic transducer to transmit ultrasonic signals onto the surface of the polishing pad through a chemical polishing slurry.

30. The method of claim 29 wherein the chemical polishing slurry comprises deionized water.

31. The method of claim 10 wherein the processing comprises generating a cross-sectional pad profile based at least in part on the reflected ultrasonic signals.

32. The method of claim 10 wherein the processing further comprises resolving approximately micron-sized properties of the polishing pad.

33. The method of claim 11 wherein the transmitting further comprises using a contact ultrasonic transducer to transmit ultrasonic signals onto the surface of the polishing pad through the deionized water.

34. The method of claim 11 wherein the processing comprises generating a cross-sectional pad profile based at least in part on the reflected ultrasonic signals.

35. The method of claim 11 wherein the processing further comprises resolving approximately micron-sized properties of the polishing pad.

36. The method of claim 17 wherein the transmitting further comprises using a contact ultrasonic transducer to transmit ultrasonic signals onto the surface of the polishing pad through a chemical polishing slurry.

37. The method of claim 36 wherein the chemical polishing slurry comprises deionized water.

38. The method of claim 17 wherein the processing comprises generating a cross-sectional pad profile based at least in part on the reflected ultrasonic signals.

39. The method of claim 17 wherein the processing further comprises resolving approximately micron-sized properties of the polishing pad.

40. The method of claim 20 wherein the transmitting further comprises using a contact ultrasonic transducer to transmit ultrasonic signals onto the surface of the polishing pad through a chemical polishing slurry.

41. The method of claim 21 wherein the transmitting further comprises using a contact ultrasonic transducer to transmit ultrasonic signals onto the surface of the polishing pad through a chemical polishing slurry.

* * * * *

UNITED STATES PATENT AND TRADEMARK OFFICE
CERTIFICATE OF CORRECTION

PATENT NO. : 7,235,488 B2  Page 1 of 1
APPLICATION NO. : 10/231801
DATED : June 26, 2007
INVENTOR(S) : Jason B. Elledge It is certified that error appears in the above-identified patent and that said Letters Patent is hereby corrected as shown below:

Column 1, line 16, change "insulting materials" to read -- insulating materials --;

line 29, change "topology" to read -- topography --; and line 37, change "topology" to read -- topography --.

Column 5, line 59, change "signals)." to read -- signals.) --.

Signed and Sealed this

Twenty-fifth Day of December, 2007

JON W. DUDAS
*Director of the United States Patent and Trademark Office*